United States Patent
Govari et al.

(10) Patent No.: US 10,974,031 B2
(45) Date of Patent: Apr. 13, 2021

(54) BALLOON CATHETER WITH INTERNAL DISTAL END

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Joseph Thomas Keyes, Glendora, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 44 days.

(21) Appl. No.: 15/857,101

(22) Filed: Dec. 28, 2017

(65) Prior Publication Data

US 2019/0201669 A1    Jul. 4, 2019

(51) Int. Cl.
*A61M 25/10* (2013.01)
*A61B 34/20* (2016.01)
*A61B 34/00* (2016.01)
*A61B 5/042* (2006.01)
*A61B 5/00* (2006.01)
*A61B 18/14* (2006.01)
*A61B 18/00* (2006.01)
*A61B 34/10* (2016.01)

(52) U.S. Cl.
CPC ....... *A61M 25/1002* (2013.01); *A61B 5/0422* (2013.01); *A61B 5/6853* (2013.01); *A61B 18/1492* (2013.01); *A61B 34/20* (2016.02); *A61B 34/25* (2016.02); *A61B 2018/0022* (2013.01); *A61B 2018/00232* (2013.01); *A61B 2018/00351* (2013.01); *A61B 2018/00357* (2013.01); *A61B 2018/00375* (2013.01); *A61B 2018/00577* (2013.01); *A61B 2018/00636* (2013.01); *A61B 2018/00791* (2013.01); *A61B 2018/00815* (2013.01); *A61B 2018/00821* (2013.01); *A61B 2018/00839* (2013.01); *A61B 2034/107* (2016.02); *A61B 2034/2051* (2016.02); *A61M 2025/1065* (2013.01)

(58) Field of Classification Search
CPC .......... A61M 2025/1065; A61M 25/10; A61B 2018/0022
See application file for complete search history.

(56) References Cited

U.S. PATENT DOCUMENTS

| 5,546,951 A | 8/1996 | Ben-Haim |
| 5,738,096 A | 4/1998 | Ben-Haim |

(Continued)

FOREIGN PATENT DOCUMENTS

| EP | 0 283 661 A2 | 9/1988 |
| EP | 2 470 248 A2 | 7/2012 |

(Continued)

OTHER PUBLICATIONS

International Search Report dated Mar. 27, 2019, International Application No. PCT/US2018/066292 (B105867W0PCT1).

*Primary Examiner* — Laura A Bouchelle

(57) ABSTRACT

A catheter adapted to slidably receive a hollow shaft through its lumen. An expandable balloon is attached to the distal portion of the hollow shaft. A nose piece disposed at the front face of the balloon forms a connection between the balloon and the distal portion of the hollow shaft. When the balloon is expanded the nose piece does not protrude beyond the front face of the balloon.

7 Claims, 4 Drawing Sheets

(56) References Cited

U.S. PATENT DOCUMENTS

| | | |
|---|---|---|
| 6,226,542 B1 | 5/2001 | Reisfeld |
| 6,301,496 B1 | 10/2001 | Reisfeld |
| 6,690,963 B2 | 2/2004 | Ben-Haim et al. |
| 6,814,733 B2 | 11/2004 | Yitzhack Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,744,594 B2 * | 6/2010 | Yamazaki ........... A61B 18/1492 604/96.01 |
| 7,756,576 B2 | 7/2010 | Levin |
| 8,478,383 B2 | 7/2013 | Bar-tal et al. |
| 9,655,677 B2 * | 5/2017 | Salahieh ............ A61B 1/00082 |
| 2006/0271040 A1 | 11/2006 | Horne et al. |
| 2007/0106320 A1 | 5/2007 | Blix et al. |
| 2007/0255209 A1 | 11/2007 | Crooms et al. |
| 2008/0215051 A1 | 9/2008 | Buysse et al. |
| 2014/0357956 A1 | 12/2014 | Salahieh et al. |
| 2014/0371778 A1 | 12/2014 | Rudakov et al. |
| 2015/0025365 A1 | 1/2015 | Esguerra Wilczynski et al. |
| 2015/0272667 A1 | 10/2015 | Govari et al. |
| 2016/0271374 A1 | 9/2016 | Spencer et al. |
| 2016/0324571 A1 | 11/2016 | Beeckler et al. |
| 2017/0354364 A1 * | 12/2017 | Bar-Tal .................. A61B 5/062 |

FOREIGN PATENT DOCUMENTS

| | | |
|---|---|---|
| EP | 3 332 727 A2 | 6/2018 |
| WO | WO 96/05768 A1 | 2/1996 |
| WO | WO 2012/087335 A1 | 6/2012 |

* cited by examiner

BALLOON CATHETER WITH INTERNAL DISTAL END

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but other-wise reserves all copyright rights whatsoever.

BACKGROUND OF THE INVENTION

1. Field of the Invention

This invention relates to medical devices. More particularly, this invention relates to a balloon catheter for transferring non-mechanical energy to and from the heart.

2. Description of the Related Art

The meanings of certain acronyms and abbreviations used herein are given in Table 1.

TABLE 1

| Acronyms and Abbreviations | |
|---|---|
| LAT | Local Activation Time |

Cardiac arrhythmias such as atrial fibrillation are a prevalent cause of morbidity and death. Commonly assigned U.S. Pat. Nos. 5,546,951, and 6,690,963, both issued to Ben Haim, and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. Nos. 6,226,542, and 6,301,496, both issued to Reisfeld, which are incorporated herein by reference.

As indicated in these patents, location and electrical activity are typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein by reference, maps depicting such motion characteristics may be constructed when the trajectory information is sampled at a sufficient number of points in the heart.

Electrical activity at a point in the heart is typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity, such as local activation times (LAT) at multiple sampled points in the heart chamber.

Procedures for treating arrhythmia include disrupting the areas causing the arrhythmia by ablation, as well as disrupting the conducting pathway for such signals. Ablation of body tissue using electrical energy is known in the art. The ablation can be performed by applying alternating currents, for example radiofrequency energy, to one or more ablation electrodes, at a sufficient power to destroy target tissue. Typically, the electrodes are mounted on the distal tip or portion of an invasive probe or catheter, which is inserted into a subject. The distal tip may be tracked in a number of different ways known in the art, for example by measuring magnetic fields generated at the distal tip by coils external to the subject.

SUMMARY OF THE INVENTION

Embodiments of the invention configure a balloon catheter so that its distal termination is inside the balloon, rather than protruding from the balloon. Having the distal termination within the balloon means the balloon has a smooth external shape.

There is provided according to embodiments of the invention a catheter adapted to slidably receive a hollow shaft through its lumen. An expandable balloon is attached to the distal portion of the hollow shaft. A nose piece disposed at the front face of the balloon forms a connection between the balloon and the distal portion of the hollow shaft. When the balloon is expanded the nose piece does not protrude beyond the front face of the balloon.

According to an additional aspect of the apparatus, when the balloon is expanded the frontal plane of the nose piece is tangential to the front face of the balloon.

According to another aspect of the apparatus, when the balloon is expanded, the front face of the balloon forms an invagination and the nose piece is disposed in the invagination.

According to one aspect of the apparatus, a proximal extension of the nose piece embraces the distal portion of the hollow shaft within the balloon.

A further aspect of the apparatus includes a magnetic coil sensor attached to the proximal extension of the nose piece.

Yet another aspect of the apparatus includes a guide wire insertable through the hollow shaft and an orifice of the nose piece.

Still another aspect of the apparatus includes a channel for introduction of fluid into the containment chamber to expand the balloon into a sphere.

According to one aspect of the apparatus, the proximal portion of the hollow shaft is attached to a control handle configured for exerting axial forces on the hollow shaft to introduce and withdraw the balloon through the lumen of the catheter.

There is further provided according to embodiments of the invention a method, which is carried out by inserting a catheter into the body of a subject, and introducing an expandable balloon through the catheter by sliding a hollow shaft through the lumen. The balloon is attached to the distal portion of the hollow shaft and has a containment chamber and a front face, a nose piece disposed at the front of the balloon forms a connection between the balloon and the distal portion of the hollow shaft. When the balloon is expanded the nose piece is non-protruding beyond the front face of the balloon.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.
Overview.

Figure 1:
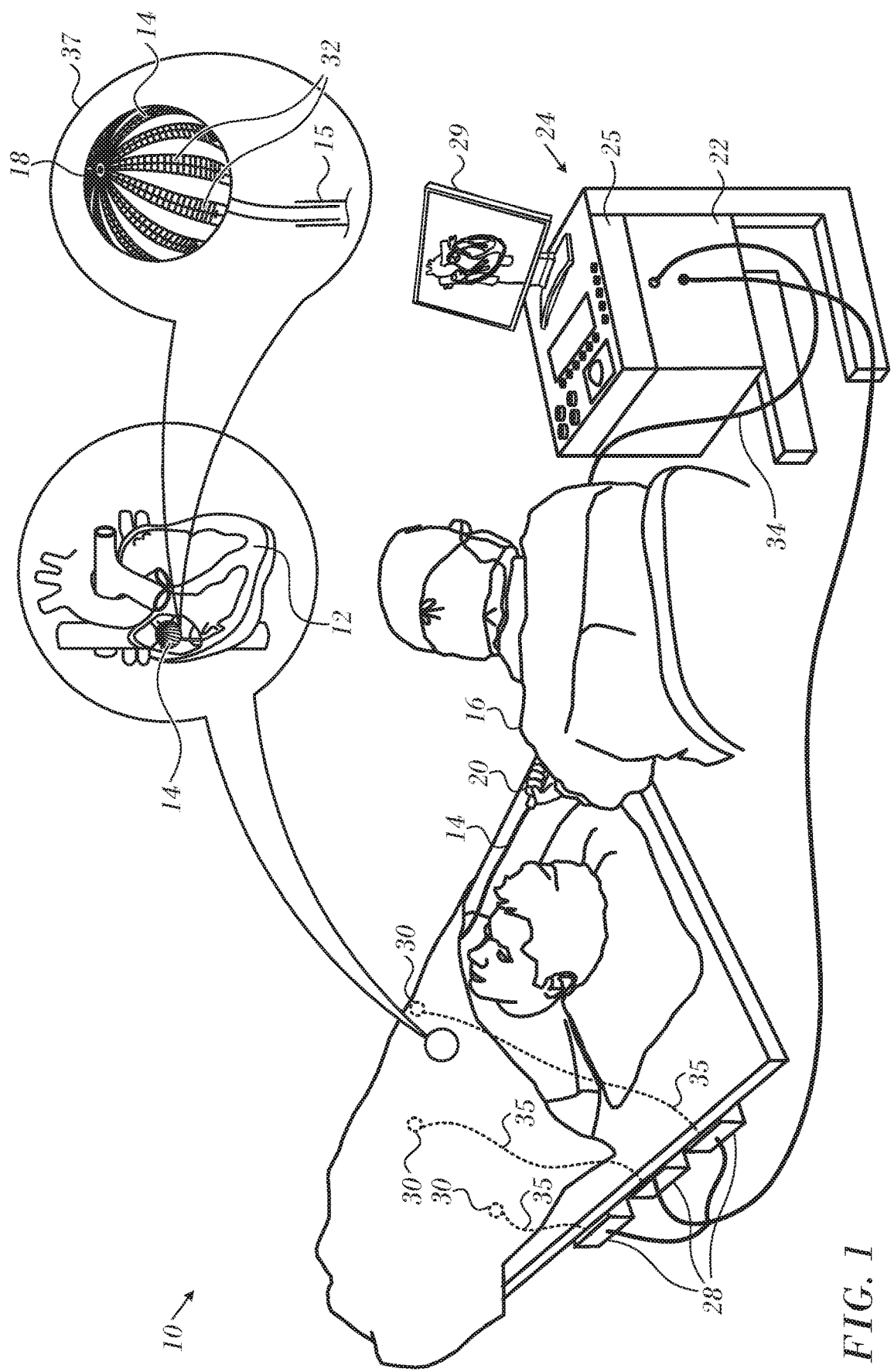
FIG. 1 is a pictorial illustration of a system for performing catheterization procedures on a heart, in accordance with a disclosed embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a multi-electrode catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 33 Technology Drive, Irvine, Calif. 92618. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains one or more position sensors (not shown) that provide signals to a processor 22, located in a console 24. The processor 22 may fulfill several processing functions as described below. As explained below, the catheter 14 is inserted by the operator 16 into the heart 12 through a sheath 15, typically via the inferior vena cava.

The catheter 14 as best seen in balloon 37 has multiple electrodes 32, which are used for sensing and ablation as described below. Once the catheter is located in the heart, by constructing a current position map, the location of each of the electrodes 32 in the heart becomes known. One method for generation of a position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22, or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted near the electrodes 32 that are used for ablation.

The console 24 typically contains one or more ablation power generators 25. The catheter 14 may be adapted to conduct ablative energy to the heart using any known ablation technique, e.g., radiofrequency energy, DC electrical energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. A suitable positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images.

Figure 2:
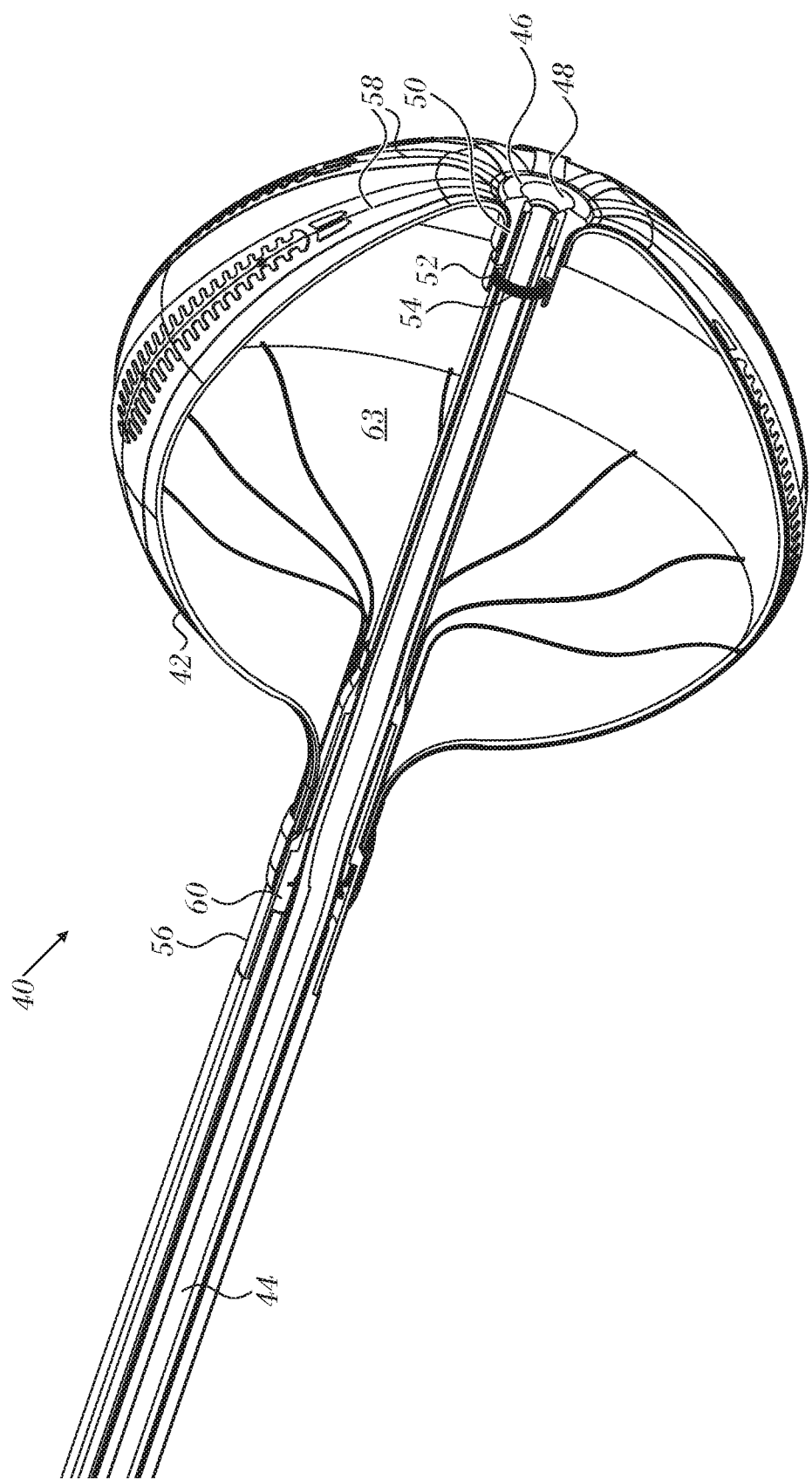
FIG. 2 is a schematic sectional view of the distal portion of an expanded balloon catheter in accordance with an embodiment of the invention.

Reference is now made to FIG. 2, which is a schematic sectional view of the distal portion of an expanded balloon catheter 40, in accordance with an embodiment of the invention. The catheter 40 has an expanded balloon 42 and central hollow shaft 44. Its purpose is to admit a lasso guide or guidewire (not shown) to aid in introducing the catheter into a desired location in the heart. This method of introduction is exemplified in commonly assigned U.S. Patent Application Publication No. 20160324571, entitled Spring-Loaded Balloon, which is herein incorporated by reference. The hollow shaft 44 is embraced distally by nose piece 46, which has an orifice 48 that communicates with the lumen of the hollow shaft 44. In this state, the nose piece 46 does not protrude above the front face of the catheter 40. In some embodiments the nose piece 46 is flush with the outer surface of the catheter 40. During manufacture the distal portion of the balloon 42 is "flipped inside-out" prior to bonding the nose piece. The balloon is blown up normally. Strips 58 are then attached to the outer surface of the balloon. The distal end of the balloon 42 is then pushed in to invert it. Adhesive is applied to the inverted surface of the balloon 42 and to the exterior of the nose piece 46. The nose piece 46 is then slid into the inverted portion and bonded to the surface of the balloon 42 to produce the configuration shown in FIG. 2.

A proximal extension 50 of the nose piece 46 embraces the hollow shaft 44 within the balloon, and has a slot 52 that holds a single axis magnetic coil sensor 54. The sensor 54 is connected via a cable (not shown) and is adapted to respond to a magnetic field produced by the field generating coils 28 (FIG. 1). It transmits location information such as deflection information to the positioning sub-system in the console 24. A catheter including single axis sensors of this sort is described in commonly assigned U.S. Patent Application Publication No. 2015/0025365, entitled Catheter with Single Axial Sensors, which is herein incorporated by reference.

Deployment.

Proximally, the balloon is bonded to a coupler 56, which loosely encloses the hollow shaft 44, enabling the hollow shaft 44 to slide through the coupler 56 to deploy the balloon. The distal end of the balloon 42 is attached to nose piece 46, which in turn is connected to the hollow shaft 44. The hollow shaft 44 extends proximally through the catheter into the handle 20 (FIG. 1), and the operator can advance or retract the hollow shaft 44 by manipulation of the handle 20. The hollow shaft 44 can slide through the coupler 56, i.e., to advance or retract the nose piece. Distal movement of the hollow shaft 44 in this manner elongates the balloon 42 and places it under axial tension. This action also forces irrigation fluid through pores (not shown) in the balloon 42.

Strips 58 contain various circuit elements, such as thermocouples, location sensors, mapping and ablation electrodes as required for a particular application. The elements communicate with console 24 (FIG. 1) via a cable (not shown).

Irrigation fluid can enter the balloon 42 via lumen 60 communicating through a fenestration (not shown) in coupler 56 leading to containment chamber 63. Introduction of fluid into the containment chamber 63 causes the balloon 42 to expand. In some embodiments the expanded balloon assumes a spherical configuration.

Although not shown in FIG. 2, the balloon 42 may be provided with pores to provide egress for the irrigation fluid, as described in commonly assigned U.S. Patent Application Publication No. 20150272667, entitled Temperature Measurement in Catheter, which is herein incorporated by reference.

First Alternate Embodiment

Figure 3:
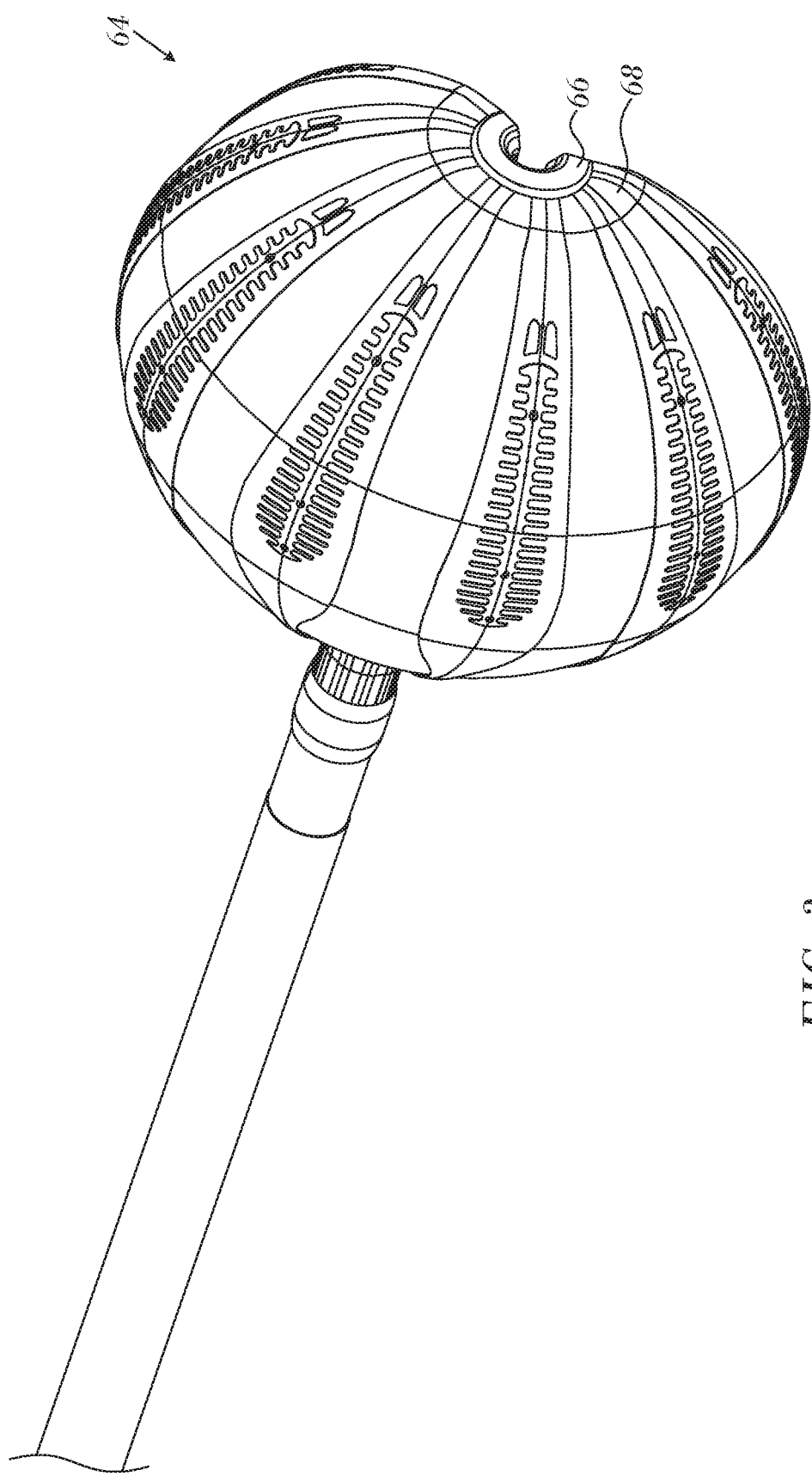
FIG. 3 is a partially cut off elevation of an expanded balloon catheter in accordance with an embodiment of the invention.

Reference is now made to FIG. 3, which is a partially cut off elevation of an expanded balloon catheter 64, in accordance with an embodiment of the invention. Nosepiece 66 is essentially flush with external surface 68 of the balloon. In this embodiment at full inflation, the balloon appears as a sphere, in which the frontal plane of the nosepiece 66 is tangential to the external surface 68.

During expansion or deflation, the nosepiece 66 is the most distal part of the catheter 64. During deflation the balloon 42 is placed under axial tension by manipulating the hollow shaft 44 using handle 20 (FIG. 1) in order to evacuate the saline or irrigation fluid. This maneuver prevents redundant balloon material from accumulating distal to the nosepiece when the balloon 42 is withdrawn into the sheath, facilitating the process.

Second Alternate Embodiment

Figure 4:
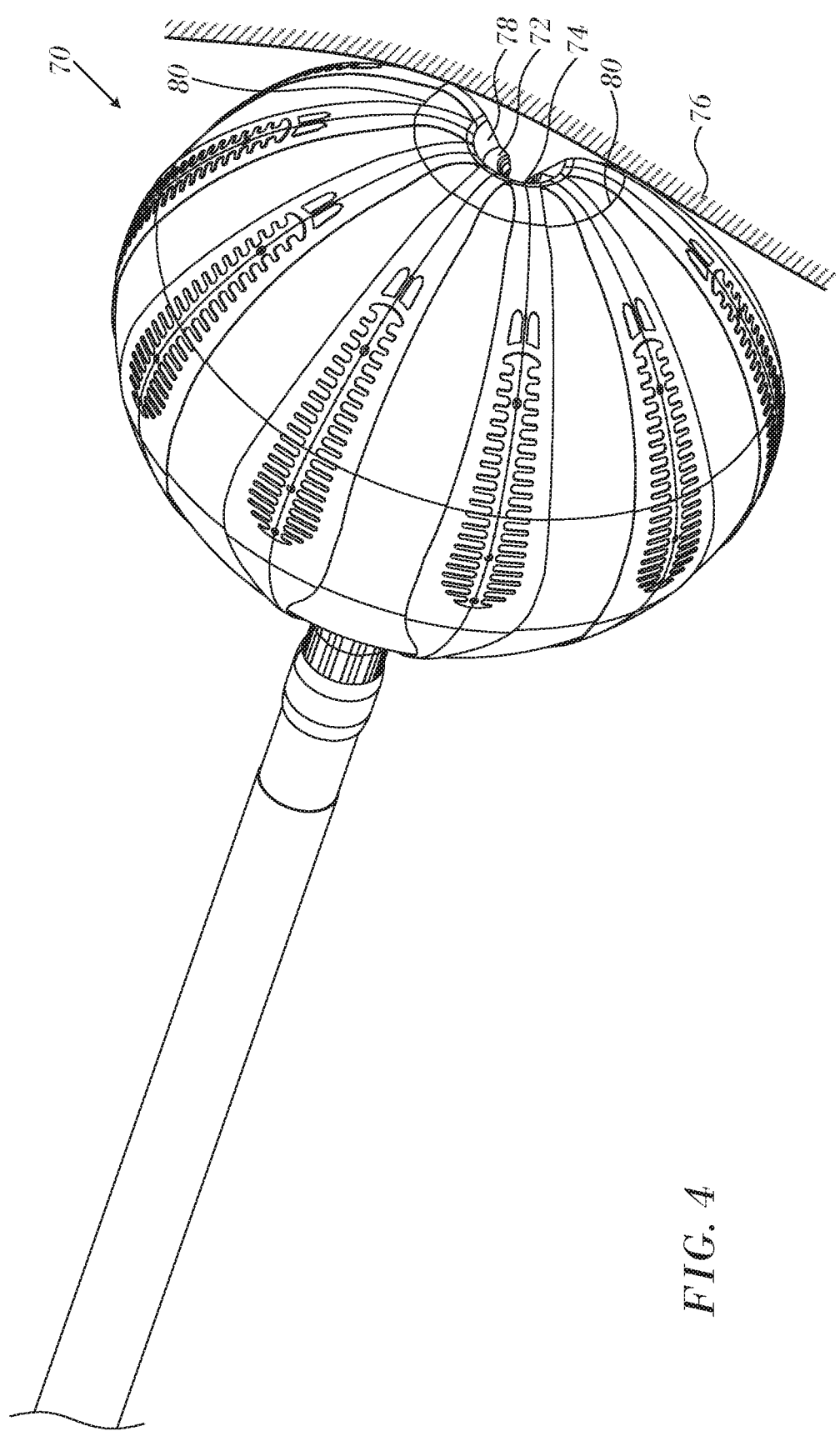
FIG. 4 is a partially cut off elevation of an expanded balloon catheter in accordance with an alternate embodiment of the invention.

Reference is now made to FIG. 4, which is a partially cut off elevation of an expanded balloon catheter 70, in accordance with an alternate embodiment of the invention. Advantageously with this embodiment, nosepiece 72 and relatively stiff guidewire lumen 74 do not contact a wall 76 of a chamber. Were they to do so, the nosepiece 72 would exert a higher force against the wall being contacted than the force exerted by the remainder of the front face of the balloon. This would cause the balloon to separate from the wall, and only the nosepiece 72 and a small portion 78 of the front face immediately around the nosepiece 72 would be in contact with the wall.

To avoid this problem the portion 78 of the front face of the balloon catheter 70 is invaginated, and nosepiece 72 is within the invagination. By invaginating the wall in this manner, only portions 80 of the balloon surface remote from the nosepiece 72 of the balloon surface contacts wall 76. The portions 80 are less stiff than the nosepiece 72 and contact the wall with a relatively uniform contact force. The nosepiece 72 and the invaginated portion 78 remains out of contact with the wall 76.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A medical apparatus, comprising:
   a catheter having a lumen;
   a hollow shaft slidable through the lumen and having a proximal portion and a distal portion;
   an expandable balloon having a containment chamber and a front face; and
   a nose piece having a proximal extension that embraces the distal portion of the hollow shaft, an orifice and a frontal plane disposed at the front face of the balloon, the proximal extension forming a connection between the balloon and the distal portion of the hollow shaft with a slot disposed on the proximal extension of the nose piece so that the slot holds a single axis magnetic coil, wherein when the balloon is expanded the nose piece is non-protruding beyond the front face of the balloon.

2. The apparatus according to claim 1, wherein when the balloon is expanded the frontal plane of the nose piece is tangential to the front face.

3. The apparatus according to claim 1, wherein when the balloon is expanded, the front face of the balloon forms an invagination and the nose piece is disposed in the invagination.

4. The apparatus according to claim 1, wherein the proximal extension of the nose piece and the hollow shaft are disposed within the containment chamber of the balloon.

5. The apparatus according to claim 1, further comprising a guide wire insertable through the hollow shaft and the orifice of the nose piece.

6. The apparatus according to claim 1, further comprising a channel for introduction of fluid into the containment chamber to expand the balloon into a sphere.

7. The apparatus according to claim 1, wherein the proximal portion of the hollow shaft is attached to a control handle configured for exerting axial forces on the hollow shaft to introduce and withdraw the balloon through the lumen of the catheter.

* * * * *